US00PP14945P2

(12) United States Plant Patent
Jepsen

(10) Patent No.: US PP14,945 P2
(45) Date of Patent: Jun. 29, 2004

(54) KALANCHOE PLANT NAMED 'KYLIE'

(50) Latin Name: *Kalanchoe blossfeldiana*
Varietal Denomination: Kylie

(75) Inventor: Knud Jepsen, Hinnerup (DK)

(73) Assignee: Knud Jepsen A/S, Hinnerup (DK)

( * ) Notice: Subject to any disclaimer, the term of this patent is extended or adjusted under 35 U.S.C. 154(b) by 0 days.

(21) Appl. No.: 10/654,489

(22) Filed: Sep. 2, 2003

(51) Int. Cl.[7] ..... A01H 5/00
(52) U.S. Cl. ..... Plt./339
(58) Field of Search ..... Plt./339

*Primary Examiner*—Bruce R. Campell
*Assistant Examiner*—Kizilkaya Michelle
(74) *Attorney, Agent, or Firm*—C. A. Whealy

(57) ABSTRACT

A distinct cultivar of Kalanchoe plant named 'Kylie', characterized by its upright plant habit; dark green-colored leaves; large light red-colored flowers; and excellent post-production longevity.

1 Drawing Sheet

Botanical classification/cultivar designation: *Kalanchoe blossfeldiana* cultivar Kylie.

BACKGROUND OF THE INVENTION

The present invention relates to a new and distinct cultivar of Kalanchoe plant, botanically known as *Kalanchoe blossfeldiana,* and hereinafter referred to by the name 'Kylie'.

The new Kalanchoe is a product of a planned breeding program conducted by the Inventor in Hinnerup, Denmark. The objective of the breeding program was to create new freely-flowering Kalanchoe cultivars with large flowers, attractive flower coloration and excellent postproduction longevity.

The new Kalanchoe originated from a cross-pollination made in Hinnerup, Denmark, of the Kalanchoe cultivar Nadia, not patented, as the female, or seed, parent with the proprietary Kalanchoe seedling selection, not patented, as the male, or pollen, parent. The new Kalanchoe was discovered and selected by the Inventor as a single flowering plant within the progeny of the stated cross-pollination grown in a controlled environment in Hinnerup, Denmark.

Asexual reproduction of the new Kalanchoe by terminal cuttings taken at Hinnerup, Denmark, by the Inventor, has shown that the unique features of this new Kalanchoe are stable and reproduced true to type in successive generations.

BRIEF SUMMARY OF THE INVENTION

The cultivar Kylie has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Kylie'. These characteristics in combination distinguish 'Kylie' as a new and distinct cultivar:

1. Upright plant habit.
2. Dark green-colored leaves.
3. Large light red-colored flowers.
4. Excellent postproduction longevity.

Plants of the new Kalanchoe differ from plants of the parents in plant size, leaf size and petal coloration.

BRIEF DESCRIPTION OF THE PHOTOGRAPHS

The accompanying colored photographs illustrate the overall appearance of the new Kalanchoe, showing the colors as true as it is reasonably possible to obtain in colored reproductions of this type. Colors in the photographs may differ slightly from the color values cited in the detailed botanical description which accurately describe the colors of the new Kalanchoe. The photographs were taken under diffuse natural light conditions on a sunny day at approximately 3:00 pm in Hinnerup, Denmark.

The photograph at the top of the sheet comprises a side perspective view of a typical potted plant of 'Kylie'.

The photograph at the bottom of the sheet comprises a top perspective view of a typical plant of 'Kylie'.

DETAILED BOTANICAL DESCRIPTION

In the following description, color reference are made to The Royal Horticultural Society Colour Chart, 1995 Edition, except where general terms of ordinary dictionary significance are used. Plants used in the photographs and for the following observations and measurements were grown in Hinnerup, Denmark, under commercial practice in a glass-covered greenhouse for about 10 weeks after the start of short day/long night photoperiodic treatment with average temperatures of 20° C. Plants used in the description and photographs were not pinched. Unless otherwise specified, the leaf description represents leaves from a vegetative plant.

Botanical classification: *Kalanchoe blossfeldiana* cultivar Kylie.

Parentage:

*Female, or seed, parent.*—*Kalanchoe blossfeldiana* cultivar Nadia, not patented.

*Male, or pollen, parent.*—Proprietary *Kalanchoe blossfeldiana* seedling selection, not patented.

Propagation:

*Type cutting.*—Terminal cuttings.

*Time to produce a rooted young plant.*—About 14 days.

*Root description.*—Numerous, fine, fibrous, and well-branched.

Plant description:

*Form.*—Upright plant habit with numerous compound cymes; freely flowering. Actual plant shape will depend on whether or not plants are pinched (apical terminals removed).

*Branching habit.*—Freely branching. Pinching (removal of terminal apex) is not required but will enhance lateral branch development.

*Plant height at flowering.*—About 26 cm.

*Plant diameter at flowering.*—About 20 cm.

*Foliage description.*—Arrangement: Opposite, simple. Size: Leaf size is reduced after floral induction. Vegetative plants: Length: About 11 cm. Width: About 8 cm. Reproduction plants: Length: About 5 cm. Width: About 4 cm. Shape: Oval. Apex: Obtuse. Base: Obtuse. Margin: Crenate; undulate. Aspect: Slightly concave. Texture: Glabrous; leathery; succulent. Color: Developing foliage, upper surface: 137A. Developing foliage, lower surface: 137B. Fully expanded foliage, upper surface: 147A. Fully expanded foliage, lower surface: 147B.

Flower description:

*Flower type and habit.*—Single flowers arranged in compound dichasial cymes that arise from leaf axils. Upright flowering stems. Freely flowering. Flowers persistent.

*Natural flowering season.*—Winter to early spring; flower initiation and development can be induced under short day/long night conditions.

*Time to flower.*—In the summer with 20° C. growing temperatures, about nine weeks of short day/long night conditions are required to produce flowering plants. During the winter with supplemental lighting and 20° C. growing temperatures, about ten weeks of short day/long night conditions are required to produce flowering plants. Time to flower is primarily dependent upon temperature and light intensity.

*Flower opening.*—First flower open is the terminal flower at the main axis and is followed by the opening of the terminal flowers of the side branches of the inflorescence. About one week after the first flower has opened, 50% of the remaining flowers are open.

*Post-production longevity.*—Plants of the new Kalanchoe maintain good leaf and flower substance for at least five weeks under interior environmental conditions.

*Flower diameter.*—About 2.4 cm.

*Quantity.*—Very freely flowering, at least 400 flowers per plant.

*Flower buds.*—Shape: Narrowly oblong. Length: About 1.6 cm. Width: About 6 mm. Color: 43B.

*Petals.*—Quantity: Four fused at base. Length: About 1.1 cm. Diameter: About 1 cm. Shape: Round obovate. Apex: Cuspidate. Margin: Entire. Texture: Glabrous, smooth and satiny. Color: Upper surface: 52A to 52B. Lower surface: Irregular areas of 155D and 52B.

*Reproductive organs.*—Stamens: Stamen number: Eight. Anther shape: Slightly oblong. Filament color: Yellow green. Pollen color: Yellow. Pistils: Pistil number: Four. Style color: Green. Stigma shape: Round. Ovaries: Superior and four-celled. Ovary size: About 8 mm by 2 mm. Ovary color: Light green.

*Seed/fruit.*—Seed and fruit production has not been observed.

Disease/pest resistance: Resistance to known pathogens and pests common to Kalanchoe has not been observed on plants of the new Kalanchoe grown under commercial greenhouse conditions.

It is claimed:

1. A new and distinct cultivar of Kalanchoe plant named 'Kylie', as illustrated and described.

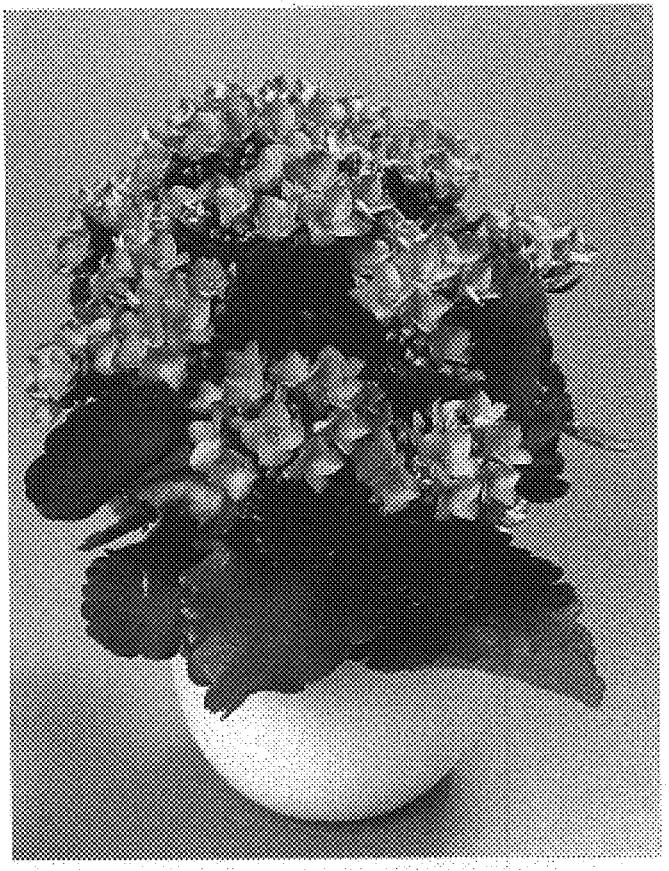
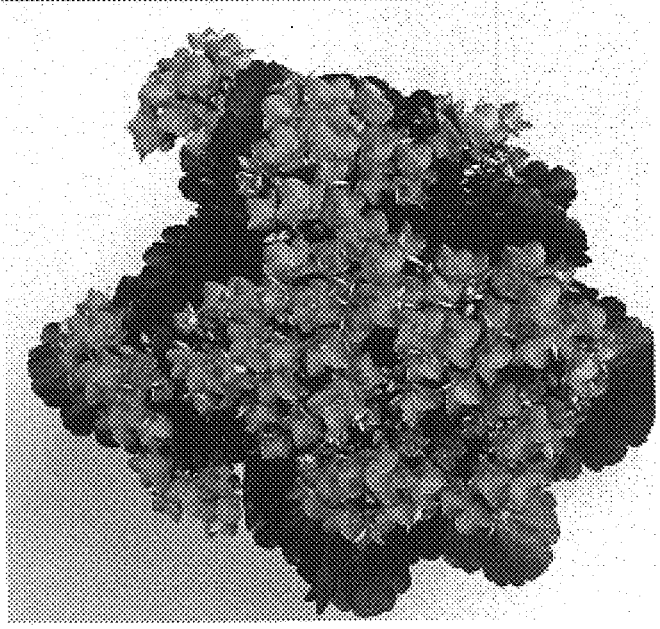

* * * * *